United States Patent
Rajala et al.

[11] Patent Number: 5,940,887
[45] Date of Patent: Aug. 24, 1999

[54] ELASTICIZED GARMENT

[75] Inventors: Gregory John Rajala, Neenah; Steven Craig Gehling, Oshkosh, both of Wis.

[73] Assignee: Kimberly-Clark Worldwide, Inc., Neenah, Wis.

[21] Appl. No.: 08/475,702

[22] Filed: Jun. 7, 1995

[51] Int. Cl.⁶ .......................... A41D 13/04; B32B 31/10; A61F 13/15
[52] U.S. Cl. .................. 2/243.1; 2/400; 2/401; 604/385.1; 604/385.2
[58] Field of Search .................. 2/400, 401, 402, 2/403, 404, 405, 406, 407, 408, 409, 79, 227, 243.1, 73, 111, 112, 274, 275; 604/385.1, 385.2, 386, 387, 393, 394, 395, 396

[56] References Cited

U.S. PATENT DOCUMENTS

| | | | |
|---|---|---|---|
| 4,402,688 | 9/1983 | Julemont | 604/385 |
| 4,430,086 | 2/1984 | Repke | 604/385 |
| 4,585,447 | 4/1986 | Karami | 604/385 A |
| 4,642,819 | 2/1987 | Ales et al. | 2/400 |
| 4,699,621 | 10/1987 | Stevens et al. | 604/385 A |
| 4,743,241 | 5/1988 | Igaue et al. | 604/385 A |
| 4,892,528 | 1/1990 | Suzuki et al. | 604/385.2 |
| 4,897,084 | 1/1990 | Ternstrom et al. | 604/385.2 |
| 5,055,103 | 10/1991 | Nomura et al. | 604/385.2 |
| 5,069,678 | 12/1991 | Yamamoto et al. | 604/385.1 |
| 5,092,861 | 3/1992 | Nomura et al. | 604/385.2 |
| 5,163,932 | 11/1992 | Nomura et al. | 604/385.2 |
| 5,171,239 | 12/1992 | Igaue et al. | 604/385.2 |
| 5,188,627 | 2/1993 | Igaue et al. | 604/385.2 |
| 5,197,960 | 3/1993 | Nomura et al. | 604/385.2 |
| 5,415,649 | 5/1995 | Watanabe et al. | 604/385.2 |

FOREIGN PATENT DOCUMENTS

| | | | |
|---|---|---|---|
| 0 073 183 A1 | 3/1983 | European Pat. Off. | A41B 9/00 |
| 0475419A1 | 3/1992 | European Pat. Off. | |
| 0487921A2 | 6/1992 | European Pat. Off. | |
| 0 692 233 A1 | 1/1996 | European Pat. Off. | A61F 13/15 |
| 3-139 349 | 6/1991 | Japan | A61F 13/54 |
| 3-139349 | 6/1991 | Japan | A61F 13/54 |
| 3139349 | 6/1991 | Japan | 604/385.1 |
| 4-28363 | 1/1992 | Japan | |
| 4-161152 | 6/1992 | Japan | A61F 13/15 |
| 404161152 | 6/1992 | Japan | 604/385.2 |
| 4-371147 | 12/1992 | Japan | A61F 13/15 |
| 404371147 | 12/1992 | Japan | 604/385.2 |
| 8024291 | 7/1994 | Japan | |
| 8-024 291 | 1/1996 | Japan | A61F 13/15 |
| 2244422 | 12/1991 | United Kingdom | |
| 2253131 | 9/1992 | United Kingdom | |
| 95/06451 A1 | 3/1995 | WIPO | A61F 13/15 |
| 96/23477 A2 | 8/1996 | WIPO | A61F 13/66 |

*Primary Examiner*—Jeanette Chapman
*Attorney, Agent, or Firm*—Jerry F. Janssen; Brian R. Tumm; Donald L. Traut

[57] ABSTRACT

This invention pertains to a three dimensional garment and subassemblies of the garment. The garment has an elasticized leg and waist openings and is stretchable about the hip and stomach regions of a user. The garment provides superior fit about the legs especially in the crotch area.

27 Claims, 2 Drawing Sheets

ELASTICIZED GARMENT

FIELD OF THE INVENTION

This invention relates to pant garments in general, more specifically to undergarments, and still more specifically to garments which incorporate an absorbent layer to provide feminine care protection or protection against incontinence.

BACKGROUND OF THE INVENTION

Regular undergarments in current use are made of cotton and/or synthetic materials. Often the synthetic panties have a cotton lined crotch and elastics that form a full leg closure. Typically, the elastic garment products are made with a single piece of elastic or two pieces which are undulated.

Concerning use of the elasticized garment by women during their menstrual flow, many women experience some leakage of menses from their pads to their undergarments. This varies from being limited to a small number of pads leaking onto only the undergarment during light flow to more prevalent leakage onto the wearer's outer clothing on pads worn during heavy flow. Normally this leakage occurs at the side of the pad, although end leakage is also a problem.

Panty liners and feminine care sanitary napkins or pads used with regular undergarments have polyethylene backings that provide some barrier properties inhibiting liquid strike through. However, if the vaginal discharge extends to the sides or the ends of the pads it can leak or seep around an edge of the pad and onto the undergarment. Such leakage can stain the undergarment. Depending upon the amount of leakage, liquid may strike through or go around the undergarment and stain outer clothing and/or bedding. Women with heavy liquid flows may use one or more maxi pads, double pads and/or tampons alone, or in combination, and change these pads and tampons frequently to prevent embarrassing, messy leakage around the edges of the pads and/or staining of outer clothing. In some cases, during their heaviest flow days, some women will restrict their activities and stay home.

Placement of maxi pads and overnight pads in the crotch of regular undergarments shows that, at best, the pads lay on the leg elastic and, at worst, overhang the leg elastics. This causes side leakage onto the undergarment and possibly onto outer clothing. Typical leakage from the pad is caused by poor fit of the pad to the body, improper positioning of the pad by the user and lack of absorbency. Leakage from the undergarment onto the outer clothing is typically due to incompatibility between the pad width and the undergarment crotch width and/or lack of barrier properties in the undergarment material around the edge portion of the pad.

SUMMARY OF THE INVENTION

This invention describes a three dimensional, disposable, discrete garment and subassemblies of the garment. The leg elastics of the invention are designed to function solely as leg elastics and not as crotch elastics.

First, the invention describes a garment blank subassembly which is a type of precursor of the garment. The subassembly has a front body portion, a back body portion, and an intermediate crotch extending from the front body portion to the back body portion and between a pair of leg cutouts for defining leg openings in the garment to be assembled from the garment blank subassembly. The front body portion has first and second front leg edge portions along the leg cutouts. The back body portion has first and second back leg edge portions along the leg cutouts. First and second crotch edge portions are disposed on opposing sides of the crotch along the leg cutouts. The front body portion has a front end of the garment blank subassembly opposite the first and second front leg edges, the back body portion has a back end of the garment blank subassembly opposite the first and second back leg edges, the front and back body portions, in combination, defining opposing first and second side edges of the garment blank subassembly. The garment blank subassembly has a length extending between the front and back ends, and a width extending between the first and second sides. The garment blank subassembly, when laid out flat, comprises a first operative layer, generally extending functionally from the front end through the crotch to the back end; an optional second layer secured to the first layer; and an elastic between and secured to at least one of the first and optional second layers, and extending continuously from a first locus adjacent the first back edge, as a first section, along the width of the garment blank subassembly, generally following the first back leg edge portion toward the crotch, as a second section across the crotch, and as a third section along the width of the garment blank subassembly generally following the second back leg edge portion, to a second locus adjacent the second back edge.

Preferably, the first and third sections of elastic are stretched when the garment blank subassembly is laid out flat, and the second section of elastic is tensioned to a degree generally equivalent to, or greater than, the elastic in the first and third sections.

The contractive force vector average of an elastic may be calculated using a number of different methods including averaging and integration of absolute forces at individual points along the elastic within a center zone. The preferred method uses at least five points along the entire length of the elastic falling within the center zone and spaced equal distance from each other. Normal methods of determining forces are used.

The product of this invention may be produced advantageously by the method and apparatus of copending application (U.S. patent application, Ser. No. 08/382,108, filed Jan. 31, 1995) which is incorporated by reference.

Second, the invention describes a garment blank subassembly which is a type of precursor of the garment. The subassembly has a front body portion, a back body portion, and an intermediate crotch extending from the front body portion to the back body portion and between a pair of leg cutouts for defining leg openings in the garment to be assembled from the garment blank subassembly. The front body portion has first and second front leg edge portions along the leg cutouts. The back body portion has first and second back leg edge portions along the leg cutouts. First and second crotch edge portions are disposed on opposing sides of the crotch along the leg cutouts. The front body portion has a front end of the garment blank subassembly opposite the first and second front leg edges, the back body portion has a back end of the garment blank subassembly opposite the first and second back leg edges, the front and back body portions, in combination, defining opposing first and second side edges of the garment blank subassembly. The garment blank subassembly has a length extending between the front and back ends, and a width extending between the first and second sides. The garment blank subassembly, when laid out flat, comprises a first operative layer, generally extending functionally from the front end through the crotch to the back end; an optional second layer secured to the first layer; and an elastic between and secured to at least one of the first and optional second layers, and extending continuously from a first locus adjacent the first front edge, as a first section, along the width of the garment blank subassembly, generally following the first front leg edge portion toward the crotch, as a second section across the crotch, and as a third section along the width of the garment blank subassembly generally following the second front leg edge portion, to a second locus adjacent the second front edge.

Third, the invention comprehends a disposable garment with a leg closure elastic system. The disposable garment comprises an outer cover having front and back body portions connected by a crotch portion, the crotch portion, when laid out flat, having a length, and at any given point along the length, and a width, the front and back body portions being connected together to form a waist opening and first and second leg openings. The outer cover of the garment comprises a first outer layer. Optionally, second inner layer is in contact with the first outer layer. One or more continuous threads of elastic is disposed between, and secured to, the first and second layers. First and third sections of the elastic extend along the first and second leg openings, thereby to form puckers about the first and second leg openings at edges thereof. A second section of the elastic extends across the crotch with a tension equal to or greater than the elastic tension in the first and third sections, essentially the width of the crotch portion in the assembly corresponds generally to the width of the crotch portion when the garment is laid out flat.

Preferably, the second inner layer has first and second sides, the elastic is disposed on the first side of the second inner layer, and the second side of the second inner layer faces the wearer's body.

In some embodiments, it is preferred that the leg elastic be disposed and secured to a first and second layer. Typically, the second layer comprises a body side liner secured to the back layer.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE PREFERRED EMBODIMENTS

The following detailed description is made in the context of an article including a disposable garment, and corresponding garment subassemblies, for holding a sanitary or incontinence pad in place as an absorbent during use of the garment. It is readily apparent, however, that the garments made using the present invention can be employed with other disposable sanitary articles, such as feminine tampons, incontinent garments, diapers, training pants, and the like.

Figure 1:
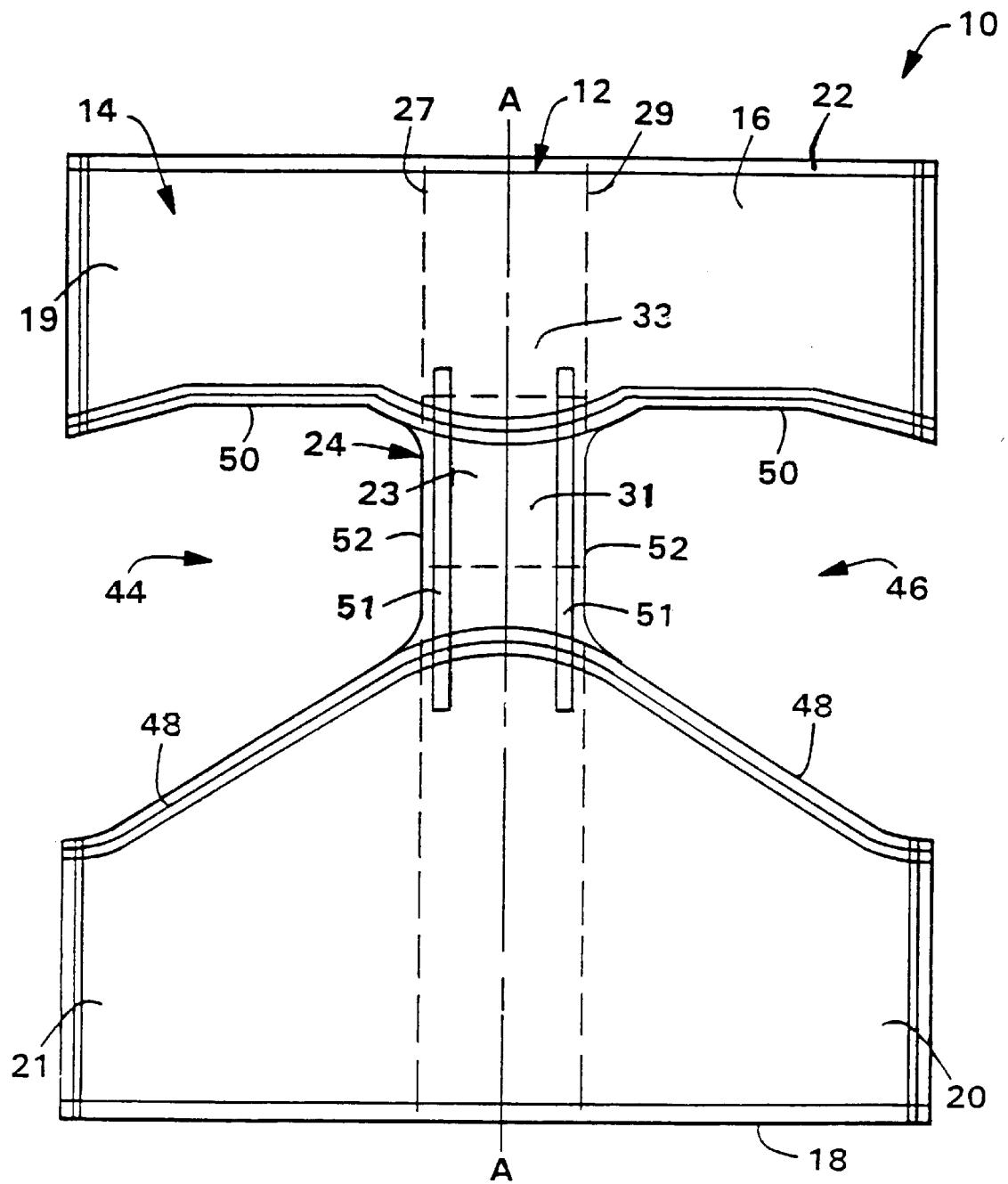
FIG. 1 is a plan view of a garment subassembly relating to an garment of the invention.

The garment subassembly 10 of FIG. 1 illustrates the preferred embodiment of the two-layer garment subassembly prior to incorporation of the absorbent. The garment subassembly of FIG. 1 illustrates the preferred embodiment of the finished garment including all elements, but before the final steps of assembling the composite to form the garment structure.

Advantageously, the body side layer 14 includes a front layer element 19 generally overlying and secured to the outer cover layer 12 on the front body portion 16, and a back layer element 21 generally overlying and secured to the outer cover layer 12 on the back body portion 20. An unsecured space 23 separates the front layer element 19 from the back layer element 21.

Referring to FIG. 1, the front body portion 16, the back body portion 20, and the crotch portion 24, in combination, form left and right leg openings 44 and 46, respectively. The leg openings 44 and 46 are formed by cutting away portions of the outer cover layer 12, and corresponding portions if any of body side layer 14. Each leg opening 44, 46 is surrounded at least in part by a back leg elastic 48, a front leg elastic 50, and a crotch elastic 51 between the back leg elastic and the front leg elastic. Each of the respective elastics 48, 50, 51 is adjacent the respective one of the edges 52 of the corresponding leg openings. The front and back leg elastics 48, 50 are secured between the outer cover layer 12 and the body side layer 14 by adhesive. The crotch elastics 51 are secured to outer cover layer 12 by adhesive. The elastics 48, 50, 51 are in the stretched state when secured to the outer cover layer 12. Accordingly, when the elastics, the outer cover layer and the body side layer are released after the elastics are secured to the outer cover layer, elastics produce leg folds or pleats at the edges of the leg openings 44, 46 to allow expansion of the leg openings 44, 46 to fit various sizes of legs. Between the front body portion and the back body portion in generally the crotch portion of the garment, an unsecured area is created. The unsecured area can be substantially unsecured or relatively unsecured in comparison to the attachment of the front and back portions to the first layer.

Figure 2:
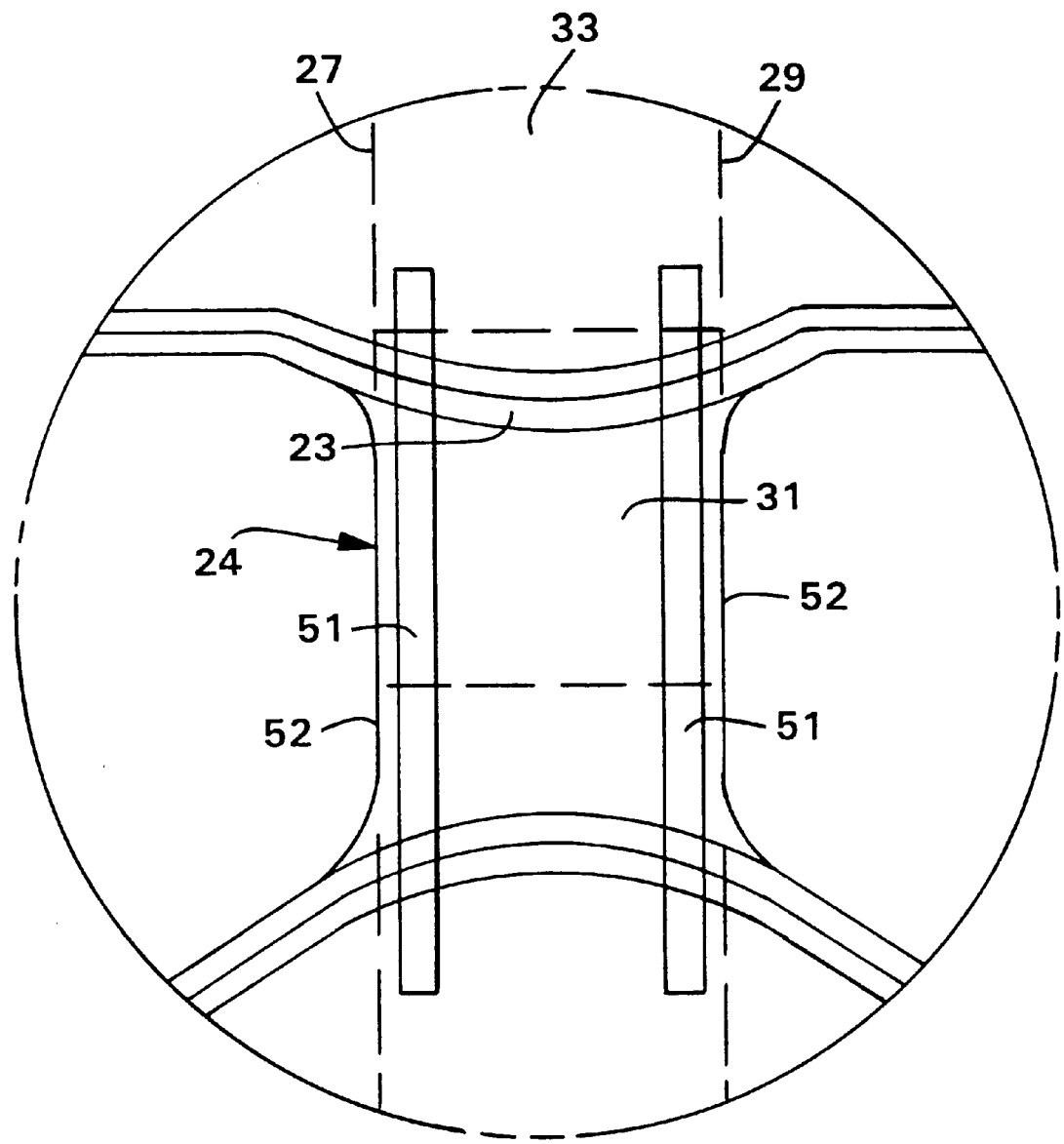
FIG. 2 is an enlarged a cut-away view of a fragment of the subassembly of FIG. 1, showing detail of the cross-crotch elastics.

Referring to FIGS. 1 and 2, a center zone 33 is designated as extending from the front end 22 to the back end 18 of the subassembly 10 delineated by a first line 27 parallel to the longitudinal centerline AA of the subassembly extending through a point on the first crotch edge 52 closest to the longitudinal centerline and a second line 29 parallel to the longitudinal centerline of the subassembly extending through a point on the second crotch edge 52 closest to the longitudinal centerline. A crotch zone 31 is defined within the center zone as a square extending from the first parallel line to the second parallel line.

The longitudinal length of the garment is measured from the front end 22 to the back end 18. The centerline of the crotch zone 31 is located such that a majority of the crotch zone 31 falls in the front half of the garment. Desirably, the centerpoint of the crotch zone is located from about 35% to about 48% of the longitudinal length from the front end 22 of the subassembly 10. More desirable the location is about 43% of the longitudinal length from the front end of the subassembly.

The width of the crotch portion 24 between the left and right crotch elastics 51 should be wide enough to accommodate laying an absorbent pad between the edges 52 without having the absorbent pad obstruct the crotch elastics 51. This allows the crotch elastics 51 to contract and draw up the sides of the crotch about the pad, to thus accommodate the thickness of the pad, and to give surface area within the crotch portion 24 of the garment, adjacent edges 52, to contain leakage from the absorbent pad.

The width of the crotch portion 24 between the elastics 51 should be wide enough to accommodate the absorbent pad, but should not be so wide as to seem bulky or uncomfortable. A suitable width is at least about 2.75 inches (70 mm)

between the crotch elastics 51. Width of crotch portion 24 is advantageous from about 3 inches (76 mm) to about 3.5 inches (89 mm). Preferably, the width is about 3 inches (76 mm).

Preferably, the crotch elastics 51 are from about 0.375 inch (10 mm) to about 0.625 inch (16 mm) wide. More preferably, the width is about 0.5 inch (13 mm). Preferably, ruffle material on the edge of the leg openings 44, 46 outside the leg elastics 48, 50 and crotch elastics 51 is less than about 0.25 (6 mm). More preferably, the ruffle material is less than about 0.125 inch (3 mm).

The overall width of the crotch portion 24 includes the width between the left and right crotch elastics 51, the width of the crotch elastics 51, and any ruffle material outside the crotch elastics 51 to the edges 52 of the leg openings. Preferably, the overall width of the crotch portion 24 should be at least about 3 inches (76 mm).

Both outer cover layer 12 and body side layer 14 are compliant and soft feeling to the wearer. The following description of materials from which the outer cover layer 12 can be made applies equally to the material of the body side layer 14.

Desirable for an absorbent product, the outer cover layer 12 may be liquid previous, permitting liquids to readily penetrate into its thickness, or impervious, resistant to the penetration of liquids into its thickness. Outer cover layer 12 may be made from a wide range of materials, such as natural fibers (e.g. wood or cotton fibers), synthetic fibers (e.g. polyester or polypropylene fibers) or from a combination of natural and synthetic fibers or reticulated foams and apertured plastic films. The outer cover layer 12 may be woven, nonwoven such as spunbonded, carded, needle punched or the like, or films. A suitable outer cover layer 12 is carded and thermally bonded by means well known to those skilled in the fabric art. Alternatively, the outer cover layer 12 is derived from a spunbonded web. In preferred embodiments, the outer cover layer 12 is spunbonded polypropylene nonwoven with a wire weave bond pattern having a grab tensile of 19 pounds as measured by ASTM D1682 and D1776, a Taber 40 cycle abrasion rating of 3.0 as measured by ASTM D1175 and Handle-O-Meter MD value of 6.6 grams and CD value of 4.4 grams using TAPPI method T402. Such spunbonded material is available from Kimberly-Clark Corporation, Roswell, Ga. The outer cover layer 12 has a weight of from about 0.3 oz. per square yard (osy) to about 2.0 osy, preferably about 0.7 osy.

The position and shape of the leg openings 44, 46 are important to avoid tightness in the crotch and groin area of the wearer, to obtain adequate buttocks coverage, and to prevent the garment 10 from tilting forward, e.g. tilting such that the front waist edge dips lower in relationship to the back waist edge. FIG. 1 illustrates the most preferred design for leg fit and buttocks coverage. The shape of the curve across the top of the leg is important. If the curve is too deep, the garment 10 will shift downward and backward resulting in a short front waist, increased back length and bagginess in the seat of the garment. This would cause the garment 10 to appear tilted when worn as evidenced by an unevenness around the waist of the wearer.

The back leg and front leg elastics 48 and 50, respectively, are attached to the garment subassembly 10, generally between the outer cover layer 12 and the body side layer 14. The crotch elastics 51 may desirably intersect the front and back elastics 48 and 50. More desirably, the crotch elastic 51 may extend outside of the crotch zone 31. The second section of back leg and front leg elastics 48 and 50 may extend substantially within crotch zone 31. Alternatively, the crotch elastic 51 may extend outside of the center zone 33 to follow the contour of the leg opening.

Materials suitable for use as the elastics include a wide variety of, but not limited to, elastic threads, yarn rubber, flat rubber (e.g. as bands), elastic tape, film-type rubber, polyurethane, and, tape-like elastomer, or foam polyurethane or formed elastic scrim. Each elastic may be unitary, multipart, or composite in construction. Threads or ribbons, where used, may be multiple and may be applied as a composite. The elastomerics used in the elastics may be latent and nonlatent.

The leg elastics 48, 50, and crotch elastic 51, including multiple threads in each, are typically about 0.5 inch (13 mm) wide. The elastic may comprise threads, ribbons, a film or composite. The threads, ribbons, etc., may be multiple and may be applied as a composite. The front leg elastics 50 and the crotch elastics 51 may be threads, preferably numbering three threads which are spaced about 0.05 to about 0.50 inch, preferably about 0.10 to about 0.20, more preferably about 0.17 inch (4.3 mm) apart. Back leg elastics 48 numbering up to six threads may have a width of about 0.75 inch (19 mm) and a thread spacing of about 0.05 to about 0.75 inch, preferably about 0.10 to about 0.20, more preferably of about 0.15 inch (3.8 mm) apart. The threads may be made of any suitable elastomeric material. One suitable material is spandex such as Lycra® threads available from Dupont, Wilmington, Del. Preferably, suitable leg elastics include threads having a total decitex (g/1000 m) of about 3760 for a 0.5 inch (13 mm) wide elastic. The decitex may vary for each element of elastics. Adhesive is used to bond the several elastics 48, 50 to the outer cover layer 12, the body side layer 14, and a support sheet.

To provide a snug leg fit and to draw up the sides of the crotch portion 24 to a cradle to receive the absorbent the leg elastics 48 and 50, and the crotch elastics 51, are elongated when applied to the layers 12 and 14 respectively. Preferably, the leg elastics 48 and 50 are applied in multiple segments, with the amount of elongation of each segment while being incorporated into the subassembly 10 being determined according to the position to be occupied by the respective segment. In the case of only front and back leg elastics, the front leg elastics 50 are advantageously elongated less than the back elastics 48. In the case of front elastics 50, back elastics 48, and crotch elastics 51, the front elastics 50 and crotch elastics 51 are preferably elongated less than the back elastics 48. Preferably, the elongation of front elastics 50 and crotch elastics 51 are minimal up to between about 100% to about 300%, preferably depending on the decitex of the elastic threads used to about 150% and the elongation of back elastics 48 along the leg openings are minimal to between about 100% to about 300% and preferably depending on the decitex of the elastic threads used to about 250%. The elongations may vary for separate elements and still be within the overall elongation for the composite of elastic elements. The differing tensions allow easier attachment of the absorbent pad, less tightness in the groin area, and less bunching of the crotch portion 24 caused by high leg elastic retraction. The back elastic 48 is under higher elongation to help keep the seat of the garment from creeping up with movement during use. In certain cases, the elongation of the front elastics 50 and back elastics 48 may be minimal when the outer layer is elastic and the front and back elastics 50 and 48 are dimensioned to be that of the minimum size of the wearer.

In the flat configuration shown for the subassembly in FIG. 1, back elastic 48 is elongated to between about 100% to about 300%, preferably depending on the decitex of the elastic threads used about 250%.

Having thus described the invention in full detail, it will be readily apparent that various changes and modifications may be made without departing from the spirit of the invention. All such changes and modifications are contemplated as being within the scope of the present invention, as defined by the following claims.

What is claimed is:

1. In a garment blank subassembly having
   a front body portion,
   a back body portion,
   a crotch intermediate of and extending from the front body portion to the back body portion and between a pair of leg openings in a garment to be assembled from the garment blank subassembly,
   the front body portion having first and second front leg edge portions along the leg openings, a front end opposite the first and second front leg edge portions along the leg openings, a front end opposite the first and second front leg edge portions and first and second front sides,
   the back body portion having first and second back leg edge portions along the leg openings, a back end opposite the first and second back leg edge portions and first and second back sides,
   the crotch having first and second crotch edge portions on opposing sides thereof along the leg openings,
   a length extending between the front and back ends,
   a width extending between the first and second sides,
   a longitudinal centerline between the first and second front and back sides,
   a center zone extending between from the front end to the back end of the subassembly and delineated by a first line parallel to the longitudinal centerline of the subassembly extending through a point on the first crotch edge closest to the longitudinal centerline and a second line parallel to the longitudinal centerline of the subassembly extending through a point on the second crotch edge closest to the longitudinal centerline,
   a crotch zone within the center zone configured as a square extending from the first parallel line to the second parallel line and having a centerpoint located such that a majority of the crotch zone falls in the front half of the subassembly,
   the garment blank subassembly, when laid out flat, comprising:
      a first elastic attached to the back body portion, and extending continuously from a first locus adjacent the first back side to a second locus adjacent the second back side comprising
         a first section along the width of the garment blank subassembly generally following the first back leg edge portion toward the center zone,
         a second section across the center zone, and
         a third section along the width of the garment blank subassembly generally following the second back leg edge portion away from the center zone,
            the second section of the first elastic having substantially the same tension as the first and third sections of the first elastic of the garment blank subassembly when the subassembly is laid out flat, wherein the contractive force vector perpendicular to the longitudinal centerline of the second section of the first elastic is greater than the contractive force vector parallel to the longitudinal centerline of the second section of the first elastic, and
      a second elastic attached to the front body portion, and extending continuously from a third locus adjacent the first front side to a fourth locus adjacent the second front side comprising
         a first section along the width of the garment blank subassembly generally following the first front leg edge portion toward the center zone,
         a second section across the center zone, and
         a third section generally following the second front leg edge portion away from the center zone,
            the second section of the second elastic having substantially the same tension as the first and third section of the garment blank subassembly when the subassembly is laid out flat, wherein the contractive force vector perpendicular to the longitudinal centerline of the second section of second elastic being greater than the contractive force vector parallel to the longitudinal centerline of the second section of the second elastic;
         wherein the second section of the first elastic is separated from the second section of the second elastic by a distance at least equal to or greater than one half of the crotch zone width; and a third elastic along the first crotch edge portion and a fourth elastic along the second crotch edge portion, wherein the third and fourth elastics intersect the second section of the first elastic.

2. The subassembly of claim 1 wherein the centerpoint of the crotch zone is located from about 35% to about 48% of the longitudinal length from the front end of the subassembly.

3. The subassembly of claim 2 wherein the centerpoint of the crotch zone is located about 43% of the longitudinal length from the front end of the subassembly.

4. The subassembly of claim 1 herein the third and fourth elastics have a contractive force, the force being divided into a vector force parallel to the longitudinal centerline of the subassembly and a vector force perpendicular to the longitudinal centerline of the subassembly, the parallel vector force being greater than the perpendicular force vector.

5. The subassembly of claim 1 wherein the third and fourth elastics have a contractive force, the force being divided into a vector force parallel to the longitudinal centerline of the subassembly and a vector force perpendicular to the longitudinal centerline of the subassembly, the parallel vector force being greater than the perpendicular force vector.

6. The subassembly of claim 1 wherein the second section of the second elastic is substantially within the crotch zone.

7. The subassembly of claim 6 wherein the third and fourth elastics extend outside the crotch zone.

8. The subassembly of claim 1 wherein the second section of the first elastic is substantially within the crotch zone.

9. The subassembly of claim 1 wherein the third and fourth elastics extend outside the center zone.

10. The subassembly of claim 9 wherein the third and fourth elastics have a contractive force, the force being divided into a vector force parallel to the longitudinal centerline of the subassembly and a vector force perpendicular to the longitudinal centerline of the subassembly, the parallel vector force being greater than the perpendicular force vector.

11. The subassembly of claim 1 wherein the second section of the first elastic is substantially within the crotch zone.

12. The subassembly of claim 11 wherein the third and fourth elastics have a contractive force, the force being divided into a vector force parallel to the longitudinal centerline of the subassembly and a vector force perpendicular to the longitudinal centerline of the subassembly, the parallel vector force being greater than the perpendicular force vector.

13. The subassembly of claim 1 wherein the second section of the second elastic is substantially within the crotch zone.

14. A garment blank subassembly having a front body portion, a back body portion, and a crotch intermediate of and extending from the front body portion to the back body portion and between a pair of leg openings in a garment to be assembled from the garment blank subassembly, the front body portion having first and second front leg edge portions along the leg openings, a front end opposite the first and second front leg edge portions along the leg openings, a front end opposite the first and second front leg edge portions and first and second front sides, the back body portion having first and second back leg edge portions along the leg openings, a back end opposite the first and second back leg edge portions and first and second back sides, the crotch having first and second crotch edge portions on opposing sides thereof along the leg openings, the garment blank subassembly having a length extending between the front and back ends, width extending between the first and second sides and a longitudinal centerline between the first and second front and back sides, a center zone extending from the front end to the back end of the subassembly and delineated by a first line parallel to the longitudinal centerline of the subassembly extending through a point on the first crotch edge closest to the longitudinal centerline and a second line parallel to the longitudinal centerline of the subassembly extending through a point on the second crotch edge closest to the longitudinal centerline, a crotch zone within the center zone configured as a square extending from the first parallel line to the second parallel line and having a centerpoint located such that a majority of the crotch zone falls in the front half of the subassembly, the garment blank subassembly, when laid out flat, comprising:
  a first elastic attached to the front portion, and extending continuously from a first locus adjacent the first front side, as a first section of the first elastic, along the width of the garment blank subassembly following the first front leg edge portion toward the center zone, as a second section of the first elastic across the center zone, and as a third section of the first elastic following the second front leg edge portion, to a second locus adjacent the second front side, the second section of the first elastic having substantially the same tension as the first and third sections of the first elastic of the garment blank subassembly when the subassembly is laid out flat, wherein the contractive force vector perpendicular to the longitudinal centerline of the second section of the first elastic is greater than the contractive force vector parallel to the longitudinal centerline of the second section of first elastic;
  a second elastic attached to the back body portion and extending from a third locus adjacent the first back side, as a first section of the second elastic, along the width of the garment subassembly following the first back leg edge portion toward the center zone, as a second section of the second elastic across the center zone and as a third section of the second elastic following the second back leg edge portion, to a fourth locus adjacent the second back side,
  wherein the second section of the first elastic is separated from the second section of the second elastic by a distance at least equal to or greater than one half of the crotch zone width; and
  a third elastic along the first crotch edge portion and a fourth elastic along the second crotch edge portion, wherein the third and fourth elastics intersect the second section of the first elastic.

15. The subassembly of claim 14 wherein the centerpoint of the crotch zone is located from about 35% to about 48% of the longitudinal length from the front end of the subassembly.

16. The subassembly of claim 15 wherein the centerpoint of the crotch zone is located about 43% of the longitudinal length from the front end of the subassembly.

17. The subassembly of claim 14 wherein the third and fourth elastics have a contractive force, the force being divided into a vector force parallel to the longitudinal centerline of the subassembly and a vector force perpendicular to the longitudinal centerline of the subassembly, the parallel vector force being greater than the perpendicular force vector.

18. The subassembly of claim 14 wherein the crotch zone has a width of at least about 70 millimeters so that the subassembly can accommodate an absorbent pad between the first and second crotch edges.

19. A garment blank subassembly having a front body portion, a back body portion, and a crotch intermediate of and extending from the front body portion to the back body portion and between a pair of leg openings in a garment to be assembled from the garment blank subassembly, the front body portion having first and second front leg edge portions along the leg openings, a front end opposite the first and second front leg edge portions along the leg openings, a front end opposite the first and second front leg edge portions and first and second front sides, the back body portion having first and second back leg edge portions along the leg openings, a back end opposite the first and second back leg edge portions and first and second back sides, the crotch having first and second crotch edge portions on opposing sides thereof along the leg openings, the garment blank subassembly having a length extending between the front and back ends, width extending between the first and second sides and a longitudinal centerline between the first and second front and back sides, a center zone extending from the front end to the back end of the subassembly and delineated by a first line parallel to the longitudinal centerline of the subassembly extending through a point on the first crotch edge closest to the longitudinal centerline and a second line parallel to the longitudinal centerline of the subassembly extending through a point on the second crotch edge closest to the longitudinal centerline, the garment blank subassembly, when laid out flat, comprising:
  (a) a first elastic attached to the front portion, and extending continuously from a first locus adjacent the first front side, as a first section of the first elastic, along the width of the garment blank subassembly following the first front leg edge portion toward the center zone, as a second section of the first elastic across the center zone, and as a third section of the first elastic following the second front leg edge portion, to a second locus adjacent the second front side,
  (b) a second elastic attached to the back-body portion, and extending from a third locus adjacent the first back side, as a first section of the second elastic, along the width of the garment blank subassembly following the first back leg edge portion toward the center zone, as a second section of the second elastic across the center zone, and as a third section of the second elastic following the second back leg edge portion, to a fourth locus adjacent the second back side, wherein the second section of the first elastic is separated from the second section of the second elastic by a distance at least equal to or greater than one half of the crotch zone width; and (c) a third elastic along the first crotch edge portion and a fourth elastic along the second crotch edge portion, the third and fourth elastics being contained within the center zone, and wherein the third and fourth elastics intersect the second section of the first elastic.

20. The subassembly of claim 19 wherein the third and fourth elastics intersect the second section of the second elastic within the center zone.

21. The subassembly of claim 19 wherein the third and fourth elastics extend outside the crotch zone.

22. The subassembly of claim 19, a crotch zone within the center zone being configured as a square extending from the first parallel line to the second parallel line and having a centerpoint located such that a majority of the crotch zone falls in the front half of the subassembly.

23. The subassembly of claim 22 wherein the centerpoint of the crotch zone is located from about 35% to about 48% of the longitudinal length from the front end of the subassembly.

24. The subassembly of claim 22 wherein the second section of the second elastic is substantially within the crotch zone.

25. The subassembly of claim 22 wherein the second section of the first elastic is substantially within the crotch zone.

26. The subassembly of claim 19 wherein the third and fourth elastics have a contractive force, the force being divided into a vector force parallel to the, longitudinal centerline of the subassembly and a vector force perpendicular to the longitudinal centerline of the subassembly, the parallel vector force being greater than the perpendicular vector force.

27. The subassembly of claim 19 wherein the crotch zone has a width of at least about 70 millimeters so that the subassembly can accommodate an absorbent pad between the first and second crotch edges.

* * * * *

UNITED STATES PATENT AND TRADEMARK OFFICE
CERTIFICATE OF CORRECTION

PATENT NO. : 5,940,887
DATED : August 24, 1999
INVENTOR(S) : Gregory J. Rajala et al.

It is certified that error appears in the above-identified patent and that said Letters Patent is hereby corrected as shown below:

Title page,
Item [57], ABSTRACT, line 2, delete "an".

Column 3,
Line 45, delete "an" and insert -- a -- in place thereof;
Line 46, after "enlarged" delete "a".

Column 5,
Line 23, delete "previous" and insert -- pervious -- in place thereof.

Claim 26,
Line 3, delete "," after the word "the".

Signed and Sealed this

Twenty-fifth Day of December, 2001

Attest:

Attesting Officer

JAMES E. ROGAN
Director of the United States Patent and Trademark Office